(12) United States Patent
Kusaki et al.

(10) Patent No.: US 8,148,053 B2
(45) Date of Patent: Apr. 3, 2012

(54) METHOD FOR MANUFACTURING SUBSTRATE FOR MAKING MICROARRAY

(75) Inventors: Wataru Kusaki, Niigata (JP); Takeshi Kinsho, Niigata (JP); Toshinobu Ishihara, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1057 days.

(21) Appl. No.: 12/073,953

(22) Filed: Mar. 12, 2008

(65) Prior Publication Data

US 2008/0233309 A1 Sep. 25, 2008

(30) Foreign Application Priority Data

Mar. 22, 2007 (JP) .................................. 2007-75309

(51) Int. Cl.
*G03F 7/26* (2006.01)
(52) U.S. Cl. ........................................ 430/324; 430/320
(58) Field of Classification Search .................. None
See application file for complete search history.

(56) References Cited

U.S. PATENT DOCUMENTS 7,285,674 B2 * 10/2007 Palma et al. .................. 556/400
(Continued)

FOREIGN PATENT DOCUMENTS

JP           A-62-050657           3/1987
(Continued)

OTHER PUBLICATIONS

Gonzalez-Leon et al; "Core-Shell Polymer Nanoparticles for Baroplastic Processing;" *Macromolecules*; vol. 38; pp. 8036-8044; 2005.

(Continued)

*Primary Examiner* — Necholus Ogden, Jr.
(74) *Attorney, Agent, or Firm* — Oliff & Berridge, Plc

(57) ABSTRACT

To provide a method for manufacturing a substrate for making a microarray which will ensure the secure immobilization of a material in a site-selective manner at a low cost. The method comprises the steps of: forming a monomolecular film on the surface of a substrate using a silane compound represented by the following general formula (1), $$Y_3Si-(CH_2)_m-X \quad (1),$$

wherein m represents an integer from 3 to 20; X represents a hydroxyl group precursor functional group which will be converted to a hydroxyl group when exposed to acid; and Y independently represents a halogen atom or alkoxy group having 1-4 carbon atoms; and converting the hydroxyl group precursor functional group represented by X to a hydroxyl group;

wherein the step of converting a hydroxyl group precursor functional group represented by X to a hydroxyl group comprises forming, on the monomolecular film, a polymer layer containing a compound represented by the following general formula (2) or (3),

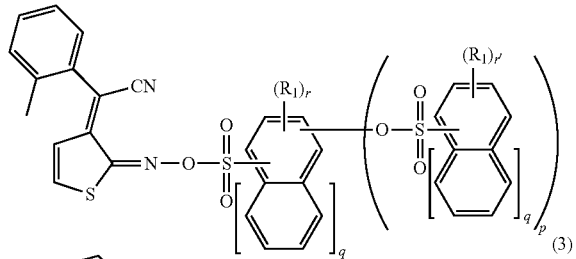

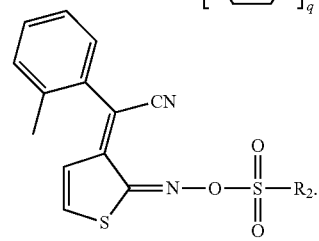

24 Claims, 1 Drawing Sheet

U.S. PATENT DOCUMENTS

2009/0005269 A1* 1/2009 Martin et al. .................. 506/32

FOREIGN PATENT DOCUMENTS

| JP | A-04-221630 | 8/1992 |
| JP | A-2005-077210 | 3/2005 |
| JP | A-2006-225476 | 8/2006 |
| JP | A-2006-328259 | 12/2006 |
| WO | WO 03/087798 A1 | 10/2003 |
| WO | WO 2007088186 * | 8/2007 |

OTHER PUBLICATIONS

Ha et al; "Preparation and Characterization of Core-Shell Particles Containing Perfluoroalkyl Acrylate in the Shell;" *Macromolecules*; vol. 35; pp. 6811-6818; 2002.

Ryu et al; "Complex Phase Behavior of a Weakly Interacting Binary Polymer Blend." *Macromolecules*; vol. 37; pp. 5851-5855; 2004.

Wallraff et al. "DNA Sequencing on a Chip;" Chemtech; pp. 22-32; Feb. 1997.

* cited by examiner

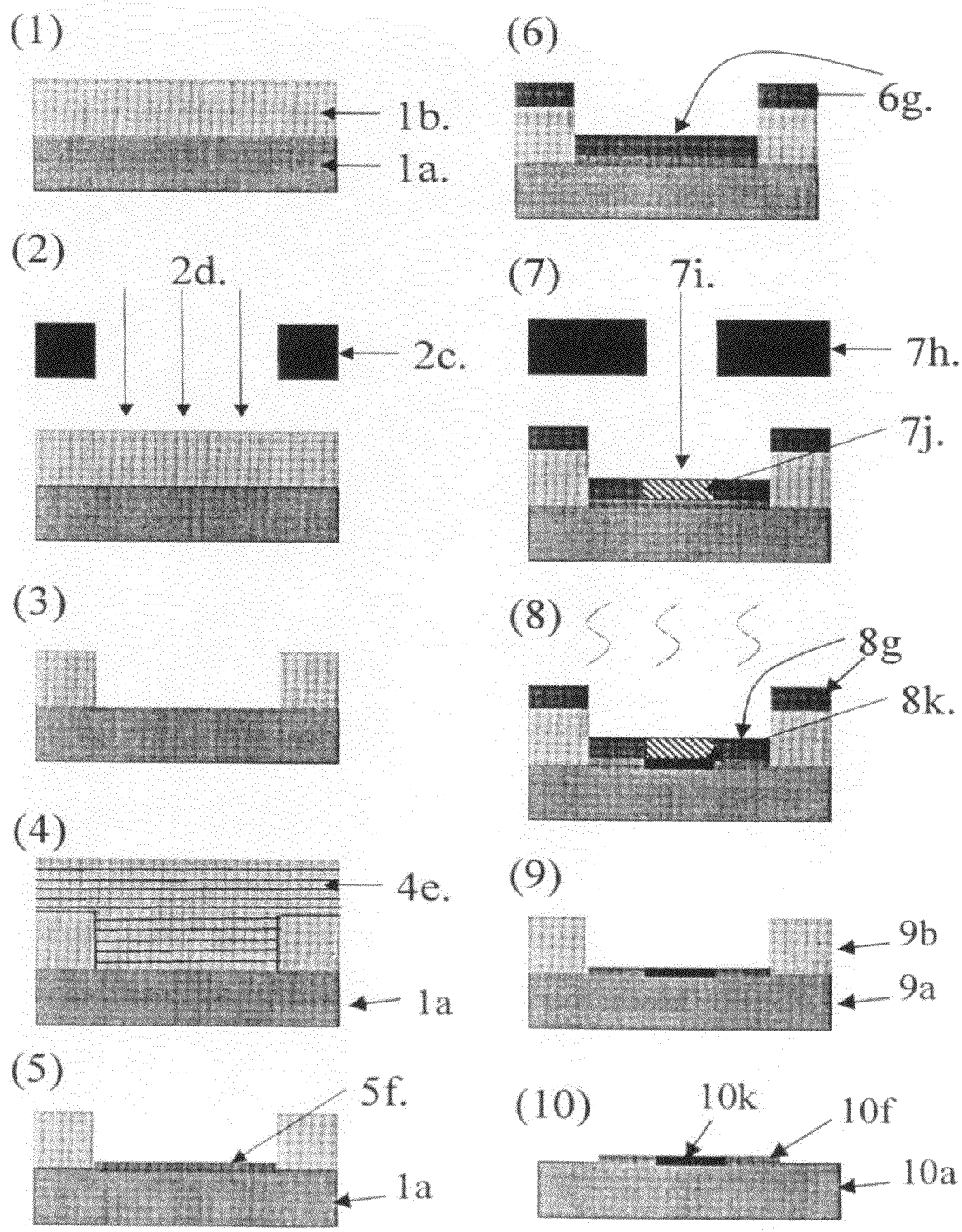

METHOD FOR MANUFACTURING SUBSTRATE FOR MAKING MICROARRAY

BACKGROUND OF THE INVENTION

1. Field of the Invention

The present invention relates to analysis technology involved in gene sequences in analyses of biologically functional molecules, particularly DNA sequences and in genetic diagnosis, and a method for manufacturing a substrate for making a device for analysis used for those analyses.

2. Description of the Related Art

Analysis of DNA sequences of genes represented by the analysis of human genome has undergone a rapid progress recently, and the information obtained by such analyses has been applied vigorously to the investigation of the functions of genes, and diagnosis of gene-mediated diseases. In parallel with this tendency, many researches have been performed on so-called DNA chips or DNA microarrays, because those chips are a powerful tool for the technique which allows the rapid and large-scale analysis of genes or study of the functions of genes.

The DNA microarray is an element wherein each of DNA molecules having specified sequences is immobilized on a tiny space so that a DNA strand in a sample having a sequence complimentary to a specified sequence can be detected. CHEMTECH, February 1997, pp. 22 proposes a method for manufacturing a DNA array based on photolithography conventionally used for the fabrication of semiconductors, wherein the site-selective synthesis of DNA sequences is carried out through a process of multiple steps so that a microarray modified by a variety of DNA molecules can be prepared after a surprisingly small number of processes. This document suggests the possibility of preparing a microarray that will allow one to examine one billion or more different kinds of DNA sequences at one time by repeating the 15-time hybridization of different nucleotides site-selectively and systematically.

On the other hand, if it were possible to electrically detect a DNA strand complimentary to a specified sequence as described above, it would be possible to analyze DNA sequences by a rapid and simple method. A number of attempts have been made for producing semiconductor apparatuses allowing for the electric detection of a DNA strand and as such known attempts, can be mentioned Domestic Re-publication of WO2003/087798 and Japanese Patent Laid-open (Kokai) No. 2005-77210. In these semiconductor apparatuses, the presence or absence of the complementary DNA strand is detected on a microchip as a practical application of a sensor by a field effect transistor known conventionally.

Incidentally, in order to prepare a DNA microarray enabling the rapid and large-scale analysis, it is necessary to immobilize DNA strands onto the tiny space of a microarray substrate site-selectively so securely that no such problems as detachment and the like can never arise. In order to analyze the biologically functional molecules including DNA molecules, as the method for two-dimensionally immobilizing them on a metal, the method of using specific absorption of a sulfur atom on a gold surface is known and described in, for example, Domestic Re-publication of WO2003/087798. Alternatively, there has been a method known for a considerably long period of time that consists of forming a monomolecular film on the surface of a substrate using silicon oxide chains, and immobilizing enzymes to the alkyl chains extending from silicon atoms in such a manner as to allow the enzymes to be immobilized to the semiconductor so securely that the risk of the molecules thus immobilized of being subject to detachment can be minimized, and Japanese Patent Laid-open (Kokai) No. 62-50657 discloses one such method. The above-mentioned Japanese Patent Laid-open (Kokai) No. 2005-77210 also mentions this method can be applied to the method it deals with.

When immobilize a material for the detection material such as a DNA molecule or peptide is immobilized onto the surface of a substrate for making a microarray, it is advisable to resort to the above-described method based on a monomolecular film comprising silicon oxide chains because the method will ensure the formation of a film comparatively free from the problems such as detachment as described above.

When it is desired to prepare a high-performance microarray, it will be necessary to achieve the site-selective immobilization of a material utilizing microlithography as indicated in CHEMTECH, February 1997, pp. 22. However, such microlithography as shown in CHEMTECH, February 1997, pp. 22 is complicated and expensive. Therefore, there is a need for a substrate for making a microarray that will allow the low-cost production and secure site-selective immobilization of a material thereto.

When it is required to immobilize a material for the detection material such as a DNA molecule or peptide on the surface of a substrate that incorporates a field effect transistor as a DNA sensor, the above-described method based on the use of a monomolecular film comprising silicon oxide chains will ensure the secure immobilization, because the method will allow the substrate to be stably placed in close proximity to the probe.

SUMMARY OF THE INVENTION

With the above-mentioned circumstance, the present invention was accomplished, and aims to provide a method for manufacturing a substrate for making a microarray which will ensure the secure site-selective immobilization of a material onto a substrate at a lower cost than is possible with the conventional method.

The present invention was accomplished to solve the above-mentioned problems, and provides a method for manufacturing a substrate for making a microarray. The method comprises at least the steps of: forming a monomolecular film on the surface of a substrate using a silane compound represented by the following general formula (1),

$$Y_3Si\text{---}(CH_2)_m\text{---}X \qquad (1),$$

wherein m represents an integer from 3 to 20; X represents a hydroxyl group precursor functional group which will be converted to a hydroxyl group when exposed to acid; and Y independently represents a halogen atom or an alkoxy group having 1-4 carbon atoms; and converting the hydroxyl group precursor functional group represented by X to a hydroxyl group, wherein the step of converting the hydroxyl group precursor functional group represented by X to a hydroxyl group comprises forming, on the monomolecular film, a polymer layer containing a compound represented by the following general formula (2), (2)

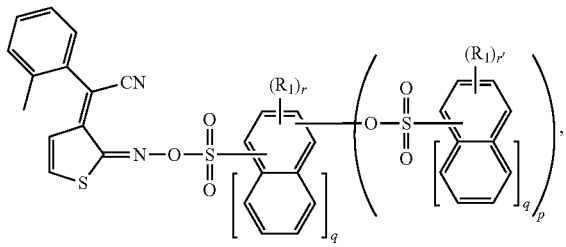

wherein $R_1$ may be the same or different, and represents a hydrogen atom, a fluorine atom, a chlorine atom, a nitro group, or a linear, branched, or cyclic alkyl group or alkoxy group having 1-12 carbon atoms substituted or unsubstituted; q independently represents 0 or 1; p is 1 or 2; r is an integer from 0 to 4; and r' is an integer from 0 to 5; or a compound represented by the following general formula (3), (3)

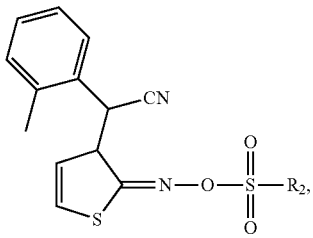

wherein $R_2$ represents a linear, branched, or cyclic alkyl group or alkoxy group having 3-10 carbon atoms substituted or unsubstituted, or a substituted or unsubstituted phenyl group or camphor; and radiating a high energy beam onto the substrate in the form of a pattern.

According to the above-mentioned method which includes forming a monomolecular film comprising an inexpensive silane compound with a hydroxyl group precursor functional group capable of efficiently reacting with generated acid, and then forming, on the monomolecular film, a polymer layer comprising a photoacid generator which efficiently generates acid when exposed to light scanned in a site-selective manner, it is possible to convert the hydroxyl group precursor functional group of a target site to a hydroxyl group through the reaction with acid generated by the photoacid generator exposed to light, and thus to site-selectively form, on the target site, a monomolecular film having a hydroxyl group securely at a low cost. If a substrate for making a microarray where each site has a monomolecular film composed as described above is used, it will be possible to immobilize a material onto any given target site of the substrate securely in a site-selective manner.

In execution of the method, the hydroxyl group precursor functional group represented by X in the general formula (1) may be an alkoxymethoxy group in which the alkoxy group moiety has 1-6 carbon atoms and/or an oxyranyl group.

Suitable examples of the hydroxyl group precursor functional group represented by X in the general formula (1), which is converted to a hydroxyl group with acid treatment, may include an alcoxymethoxy group in which the alkoxy group moiety has 1-6 carbon atoms and/or an oxyranyl group.

With regard to the step of forming a monomolecular film using a silane compound represented by the general formula (1), it is preferred to mix the silane compound with at least one or more silane compounds represented by the following general formulae (4) and (5):

$$Y'_3Si-(CH_2)_n-CH_3 \quad (4)$$

$$Y'_3Si-(CH_2)_n-OCH_3 \quad (5)$$

wherein n is an integer from 0 to (m-2), m is as defined in relation to the general formula (1); and Y' represents a halogen atom or an alkoxy group having 1-4 carbon atoms; and use the resulting mixture to form the monomolecular film.

When at least one or more of silane compounds represented by the general formulae (4) and (5) is combined with a silane compound represented by the general formula (1) into a mixture and the mixture is used for the formation of a monomolecular film, it is possible to dispose hydroxyl groups which are necessary for the immobilization of a material outwards from the average surface of the monomolecular film, and thus to ensure a space around each site sufficiently wide for the immobilization of a material. Through this arrangement it is possible to securely execute the immobilization operation, to ensure a blank space around a material immobilized to the site and to securely detect, during the actual practice of analysis, the presence of a test sample if any by virtue of the material immobilized to the site.

Furthermore, it is preferred to combine a compound represented by the general formula (5) with a compound represented by the general formula (4) into a mixture, and to use the mixture, because then it is possible to add the mixture to a silane compound represented by the general formula (1) for mixture advantageously without being accompanied by the increase of contact angle.

In relation to the step of converting a hydroxyl group precursor functional group to a hydroxyl group, it is preferred to form a polymer layer comprising a photoacid generator on the substrate and then subject the substrate to heating treatment, radiate a high energy beam onto the substrate in the form of a pattern and then subject the substrate to heating treatment, and then remove the polymer layer.

When heating treatment is introduced after a polymer layer has been formed on a substrate by means of a photoacid generator as described above, it is possible to vaporize the solvent through the heating treatment, and immobilize a material onto the surface of the substrate, which makes the handling of the substrate easy during the succeeding operations, particularly during exposure to light. Further, when heating treatment is introduced after a high energy beam has been radiated onto the substrate, it will allow the hydroxyl group precursor functional group present on the surface of the monomolecular film to complete a reaction with generated acid, or promote the reaction.

It is preferred to select a high energy beam having a wavelength in the range of 250 nm to 400 nm.

When the high energy beam having a wavelength in the range of 250 nm to 400 nm is used, the risk of severing the bond of a silane compound forming a monomolecular film to a substrate which would result in the detachment of the silane compound from the substrate will be minimized.

The microarray can be used for analyses of biomolecules.

Furthermore, the present invention can provide the method for manufacturing a substrate for making a microarray wherein the method further contains a step that on the substrate in which the hydroxyl group generated through the step of converting the hydroxyl group precursor functional group of the silane compound into a hydroxyl group has been attached, in a dehydrated environment, a mononucleotide which has its 5'-end protected with an acid leaving group and 3'-end with phosphoramidite attached, and the acid leaving group attached to the 5'-end is converted into a hydroxyl group using the photoacid generator as described above contained in a polymer layer.

The acid leaving group for protecting the 5'-end of the nucleotide is preferably a dimethoxytrityl group.

Namely, the method of the present invention for making a microarray by means of a monomolecular film and a photoacid generator can be applied to the oligonucleotide extension method.

The microarray may be used in tests involving the sequencing of genes including the analysis of biologically functional molecules, particularly of DNA sequences, and genetic diagnosis.

As described above, it is possible to securely obtain a substrate for making a microarray at a low cost which has hydroxyl groups arranged thereon in a site-selective manner by employing the method for manufacturing a substrate for making a microarray of the present invention.

BRIEF DESCRIPTION OF THE DRAWINGS

FIG. 1 is a diagram for outlining an embodiment of a method for manufacturing a substrate for making a microarray according to the present invention.

REFERENCE NUMERALS

1a: Substrate
1b: Resist film
2c: Patterned mask
2d: Excimer laser beam
4e: Solution for the formation of a monomolecular film
5f: Monomolecular film
6a: Substrate for the manufacture of microarray
6g: Polymer layer
7h: Patterned mask
7i: i-beam
7j: Irradiated site in polymer layer
8k: Site at which conversion into hydroxyl group occurs in a monomolecular film
8g: Polymer layer
9a: Substrate
9b: Resist film
10a: Substrate for the manufacture of microarray
10k: Site at which immobilization of a detection material occurs
10f: Monomolecular film

DESCRIPTION OF THE INVENTION AND A PREFERRED EMBODIMENT

The present invention will be described below with reference to embodiments, but it should be understood that the present invention is not limited to those embodiments.

The present inventors had thought, in order to develop hydroxyl groups on the surface of a substrate in a site-selective manner, it is necessary to select a hydroxyl group precursor functional group as a functional group of a silane compound constituting a monomolecular film to be formed on the substrate so that efficient reaction with generated acid can be ensured, and to select a photoacid generator which can efficiently generate acid when exposed to light scanned in a site-selective manner.

With a view to achieve the object, the present inventors studied hard and accumulated investigation data to reach a finding that what is mandatory is the intervention of a monomolecular film having a silicon oxide chain comprising a hydroxyl group precursor functional group as a functional group which will be securely converted to a hydroxyl group through a single step reaction, and the selection of a photoacid generator which will efficiently generate acid when exposed to light. The inventors found that the finding solves the problems, to achieve the present invention.

That is, the present invention provides a method for manufacturing a substrate for making a microarray which comprises the steps of: forming a monomolecular film on the surface of a substrate using a silane compound represented by the following general formula (1),

$$Y_3Si-(CH_2)_m-X \quad (1),$$

wherein m represents an integer from 3 to 20; X represents a hydroxyl group precursor functional group which will be converted to a hydroxyl group when exposed to acid; and Y independently represents a halogen atom or a alkoxy group having 1-4 carbon atoms; and converting the hydroxyl group precursor functional group represented by X to a hydroxyl group, wherein the step of converting a hydroxyl group precursor functional group represented by X to a hydroxyl group comprises forming, on the monomolecular film, a polymer layer containing a compound represented by the following general formula (2),

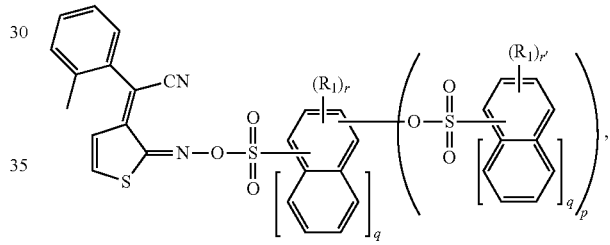

wherein $R_1$ may be the same or different, and represents a hydrogen atom, a fluorine atom, a chlorine atom, a nitro group, or a linear, branched, or cyclic alkyl group or alkoxy group having 1-12 carbon atoms substituted or unsubstituted; q independently represents 0 or 1; p is 1 or 2; r is an integer from 0 to 4; and r' is an integer from 0 to 5; or a compound represented by the following general formula (3),

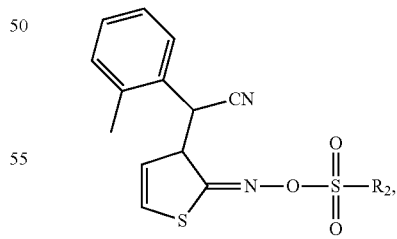

wherein $R_2$ represents a linear, branched, or cyclic alkyl group or alkoxy group having 3-10 carbon atoms substituted or unsubstituted, or a substituted or unsubstituted phenyl group or camphor; and radiating a high energy beam onto the substrate in the form of a pattern.

The microarray prepared according to the method for manufacturing a substrate for making a microarray of the present invention is not limited, with regard to its data acquisition methodology, to any particular method including a fluorescence-based method, electricity-based method, or the like, but when the method of the present invention is employed on a semiconductor apparatus during the preparation of a substrate for making a microarray, it is particularly preferred.

When the analysis is performed by the electric method using the semiconductor apparatus, as the semiconductor apparatus, the method of immobilizing on a capacitor as shown in Domestic Re-publication of WO2003/087798 and the method of immobilizing to a gate electrode or the surface of a floating electrode connected to the gate electrode as shown in Japanese patent Laid-open (Kokai) No. 2005-77210 are known.

In the practice of the method of the present invention, when the top surface of a substrate material responsible for the immobilization is constituted of a metal oxide film, it is possible to form a monomolecular film having silicon oxide chains on the substrate by directly treating the top surface with a silicon compound as described later, since the metal oxide contains a sufficient amount of hydroxyl group. Alternatively, when the top surface of a substrate is constituted of a metal film, a superficial oxide layer naturally forming on the metal film may be used, or only the superficial layer of the metal film may be deliberately oxidized by exposing it to ozone, aqueous solution of hydrogen peroxide, water, or oxygen plasma, and the like. When detection is achieved by a method not dependent on electricity, the monomolecular film may be formed on a resin substrate. In such a case, according to the disclosure given by Japanese Patent Laid-open (Kokai) No. 4-221630, it is possible to form a monomolecular layer comprising silicon oxide chains by exposing the surface of the substrate to an electron or ion beam in an oxygen atmosphere.

The monomolecular film may be formed over the entire surface of a substrate. However, generally, the monomolecular layer may be formed on desired positions over the surface of a substrate. This may be achieved by using a resist film so that positions of a monomolecular film are formed site-selectively over the substrate. The operation for this has been known well in the art, and the suitable resist film is not limited to any known specific one, but it is preferred to use a chemically amplified type resist because such a resist may allow a monomolecular film to be formed on tiny positions precisely in a site-selective manner.

As the chemically amplified resist used here, it is preferable that the monomolecular film is not formed on the resist film in the step of forming the monomolecular film. It is preferable that the resin used for the resist composition contains 5 mole % or less polymerization unit containing hydroxyl group. It is more preferable that the unit having the hydroxyl group is not contained. Thus, also in this sense, it is preferable to select the chemically amplified positive resist rather than a novolak based resist where the presence of the hydroxyl group is essential on its mechanism or a negative type resist where solubility is changed by crosslinking based on the hydroxyl group, as the type of the resist.

A preferred resin suitably used for the construction of a positive resist which does not require the introduction of hydroxyl group for its polymerization mechanism in contrary to the polymers as mentioned above, is a polymer obtained by combining a unit having an acid functional group protected by an acid degradable protecting group with a so-called adhesive group generated for the combined use of an ArF excimer laser.

The unit having an acid functional group protected with an acid degradable protecting group may include a tertiary alkyl group, tertiary alkoxycarbonyl group, or a unit having phenolic OH protected with acetal group, more specifically protected vinylphenol, similarly protected carboxyl group, more specifically protected vinyl benzoate, (metha)acrylate, and the like. Many of them have been known in the prior art (see, for example, Japanese Patent Laid-open (Kokai) No. 2006-225476 and Japanese Patent Laid-open (Kokai) No. 2006-328259).

The so-called adhesive group which has been generated for the use in combination with an ArF excimer laser may include units which include a cyclic ether structure or lactone structure. Particularly, those that have a lactone structure are notably effective, and many of them have been known in the prior art (see, for example, Japanese Patent Laid-open (Kokai) No. 2006-328259).

With regard to the polymerization ratio of the two units described above, when the unit having an acid functional group protected with an acid degradable protecting group is used at 20 mole % or more, the resulting film will be nearly relieved of the risk of degrading the resolution. On the other hand, when the unit having an adhesive group is used at 40 mole % or more, the resulting film will be nearly relieved of the risk of being dissociated from the substrate.

To a composition for the formation of a resist film, may be added as needed a basic substance, a surfactant and the like, and many of such additives have been known in the prior art (see, for example, Japanese Patent Laid-open (Kokai) No. 2006-225476 and Japanese Patent Laid-open (Kokai) No. 2006-328259), and basically any of them may be used. Further, methods for the formation of a resist pattern have been known in the prior art, and it is possible to use any of those methods such that only desired portions can be masked.

The step of forming a monomolecular film having silicon oxide chains comprises treating an uncoated substrate, that is, when the substrate has a resist pattern formed on its surface for protecting the portions other than positions where a detection material will be immobilized, the surface of those positions, and when the substrate having no resist pattern formed thereon so that a detection material can be immobilized on the entire surface, the entire surface, with a solution containing a silane compound represented by the following general formula (1),

$$Y_3Si\text{—}(CH_2)_m\text{—}X \qquad (1),$$

wherein m represents an integer from 3 to 20; X represents a hydroxyl group precursor functional group which will be converted to a hydroxyl group when exposed to acid; and Y independently represents a halogen atom or an alkoxy groups with 1 to 4 carbon atoms; and forming thereby a monomolecular film on the substrate.

When m of the general formula (1) is 3 or more, the resulting compound will be satisfactory, as far as the formation of a monomolecular film is concerned. However, as will be described later, when it is required to precisely define positions where detection materials will be immobilized, the compound where m is equal to or larger than 5, or more preferably m is equal to or larger than 8 should be used.

The hydroxyl group precursor functional group X' is the hydroxyl group protected with the so-called protecting group or vicinal diol. Many of such protecting groups are known publicly, and representatives thereof can include acyl, oxyranyl and acetal groups. In the later step, the particular region on the monomolecular film is masked using the resist in order to immobilize the material for recognition to only the particular region on the resulting monomolecular film. When the chemically amplified type resist is used here, it is preferable that the monomolecular film is not contaminated with the basic substance and capable of being deprotected by acidic treatment. Those capable of being deprotected under an acidic condition include oxyranyl and acetal groups in the above. Among the acetal groups, when X' is a methoxymethoxy group or an oxyranyl group, the monomolecular film is easily formed because the groups are sterically small.

The hydroxyl group which serves as a functional group responsible for the immobilization of a detection material should have a sufficient space around it as easily expected from its function. To introduce such an environment, it is preferred to mix the silane compound represented by the general formula (1) with at least one or more of silane compounds having shorter chains and represented by the following general formulae (4) and (5),

wherein n is an integer from 0 to (m-2), m is as defined in relation to the general formula (1); and Y' represents a halogen atom or an alkoxy group having 1-4 carbon atoms; and use the resulting mixture. The compound(s) represented by the general formula (4) and/or (5) may be added by 1 mole times or more, or more preferably 4 mole times or more than the silane compound represented by the general formula (1). To ensure the immobilization of a sufficient amount of a detection material, however, the former compound is preferably added at 200 mole times or less, more preferably 100 mole times or less.

Formation of a monomolecular film comprising a silane compound having silicon oxide chains may be achieved by a method as disclosed in Japanese Patent Laid-open (Kokai) No. 62-50657. Namely, formation of a monomolecular film may be achieved by employing, for example, a solvent having a very low polarity, adding the solvent to a silane compound represented by the general formula (1), and further adding at least one or more chosen from the silane compounds represented by the general formulae (4) and (5) to give a comparatively dilute solution where the mixture is present at $2.0 \times 10^{-2}$ to $5.0 \times 10^{-2}$ mole/l. Then, a coated substrate where portions of its surface which should reject the formation of a film have been protected with a resist, is immersed in the solution. For example, when trichlorosilane is used as the solvent, the preferred immersion time will be 2 to 3 minutes, while when trimethoxysilane is used, the time in question will be 2 hours.

When a monomolecular film is formed on a substrate as described above, and the step is introduced for converting the hydroxyl group precursor functional group represented by X into a hydroxyl group, a substrate for making a microarray is obtained whose surface is coated with a monomolecular film comprising silicon oxide chains having hydroxyl group as a functional group responsible for the immobilization.

In order that conversion of the hydroxyl group precursor functional group into a hydroxyl group (deprotection) can occur on the substrate in a site-selective manner, the method of the present invention, after a polymer layer containing a specified photoacid generator has been formed on the monomolecular film, radiates a high-energy beam onto the substrate in the form of a pattern.

The specified photoacid generator to be contained in a composition for the formation of the polymer layer may include compounds represented by the following general formulae (2) and (3).

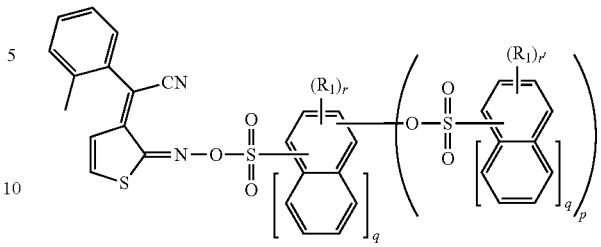

In the formula, $R_1$ may be the same or different, and represents a hydrogen atom, a fluorine atom, a chlorine atom, a nitro group, or a linear, branched, or cyclic alkyl group or alkoxy group having 1-12 carbon atoms substituted or unsubstituted; q independently represents 0 or 1; p is 1 or 2; r is an integer from 0 to 4; and r' is an integer from 0 to 5.

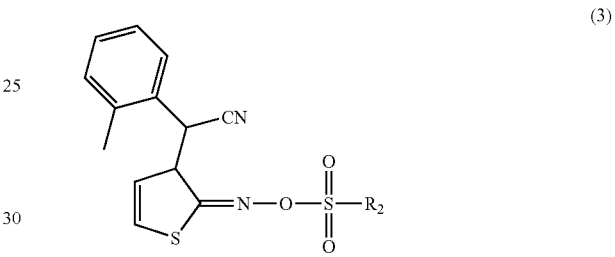

In the formula, $R_2$ represents a linear, branched, or cyclic alkyl group or alkoxy group having 3-10 carbon atoms substituted or unsubstituted, or a substituted or unsubstituted phenyl group or camphor.

With regard to the general formula (2), $R_1$ may be the same or different, and represents a hydrogen atom, a fluorine atom, a chlorine atom, a nitro group, or a linear, branched, or cyclic alkyl group or alkoxy group having 1-12 carbon atoms substituted or unsubstituted, and may include, for example, a hydrogen atom, a methyl group, an ethyl group, a n-propyl group, a sec-propyl group, a cyclopropyl group, a n-butyl group, a sec-butyl group, an iso-butyl group, a tert-butyl group, a methoxy group, an ethoxy group, a n-propyloxy group, a sec-propyloxy group, n-butyloxy group, a sec-butyloxy group, an iso-butyloxy group, a tert-butyloxy group, an n-hexyl group, an n-hexyloxy group, an n-octyl group, an n-octyloxy group, an n-decyl group, an n-decyloxy group, an n-dodecyl group, an n-dodecyloxy group and the like. Among them, a hydrogen atom, methyl group, an ethyl group, an n-hexyloxy group, or an n-octyloxy group may be preferably used. In particular, a hydrogen atom, or a methyl group may be used more preferably. q independently represents 0 or 1, and p is 1 or 2. r is an integer from 0 to 4, and r' an integer from 0 to 5. Substitution by arylsulfonyloxy group of allenesulfonyl group is not limited to any specific position, but may occur at any position. However, when the allenesulfonyl group is benzenesulfonyl group, substitution may preferably occur at the fourth position, and when the allenesulfonyl group is naphthalenesulfonyl group, the preferred position of substitution varies depending on the kind of naphthalenesulfonyl group: the fourth, fifth, or eighth position may be preferred when the naphtalenesulfonyl group is 1-naphthalenesulfonyl group while the sixth position may be preferred when the naphthalenesulfonyl group is 2-naphthalenesulfonyl group.

More specifically, preferred (arylsulfonyloxy)allenesulfonyloxy groups may include 4-(4'-toluenesulfonyloxy)benzenesulfonyloxy group, 4-(benzensulfonyloxy)benzenesulfonyloxy group, 4-(4'-methoxybenzenesulfonyloxy) benzenesulfonyloxy group, 4-(4'-fluorobenzenesulfonyloxy) benzenesulfonyloxy group, 4-(4'-trifluoromethylbenzenesulfonyloxy)benzenesulfonyloxy group, 4-(pentafluorobenzenesulfonyloxy)benzenesulfonyloxy group, 4-(2-naphthalenesulfonyloxy)benzenesulfonyloxy group, 3-methoxy-4-(4'-toluenesulfonyloxy)benzenesulfonyloxy group, 3-methyl-4-(4'-toluenesulfonyloxy)benzenesulfonyloxy group, 2-(4'-toluenesulfonyloxy) naphthalene-6-sulfonyloxy group, 1-(4'-toluenesulfonyloxy) naphthalene-4-sulfonyloxy group, 1-(4'-toluenesulfonyloxy) naphthalene-8-sulfonyloxy group, 2,5-bis(4'-toluenesulfonyloxy)benzenesulfonyloxy group, 2,5-bis(4'-methoxybenzenesulfonyloxy)benzenesulfonyloxy group, and the like, but are not limited to them.

With regard to the general formula (3), $R_2$ may include a linear, branched, or cyclic alkyl group or alkoxy group having 3-10 carbon atoms substituted or unsubstituted, or more specifically an n-propyl group, a sec-propyl group, cyclopropyl group, an n-butyl group, a sec-butyl group, an iso-butyl group, a tert-butyl group, methoxy group, an ethoxy group, an n-propyloxy group, a sec-propyloxy group, an n-butyloxy group, a sec-butyloxy group, an iso-butyloxy group, a tert-butyloxy group, an n-hexyl group, an n-hexyloxy group, an n-ocytyl group, an n-octyloxy group, an n-decyl group, an n-decyloxy group, and the like. Or, $R_2$ represents a substituted or unsubstituted phenyl group or camphor, more specifically, a phenyl group, a p-methylphenyl group, or camphor.

The photoacid generator as described above is preferable because it will generate acid when exposed to light having a wavelength in the range of 250 nm to 400 nm.

The polymer to be used as a material for forming the polymer layer may include any polymer, as long as it is permeable to a high-energy beam and is miscible to the photoacid generator.

The material to be used for the formation of the polymer layer may further include any one or more of organic solvent, basic compound and surfactant.

The organic solvent suitably used in the present invention may include any organic solvent, as long as it allows the dissolution of a polymer, acid generator, and other additives. Such organic solvents may include, for example, ketones such as cyclohexanone, methyl-2-n-amyl ketone, and the like; alcohols such as 3-methoxybuthanol, 3-methyl-3-methoxybuthanol, 1-methoxy-2-propanol, 1-ethoxy-2-propanol, and the like; ethers such as propyleneglycol monomethylether, ethyleneglycol monomethylether, propyleneglycol monoethylether, ethyleneglycol monoethylether, propyleneglycol dimethylether, diethyleneglycol dimethylether, and the like; esters such as propyleneglycol monomethylether acetate, propyleneglycol monoethylether acetate, ethyl lactate, ethyl pyruvate, butyl acetate, 3-methoxypropionic acid methyl, 3-ethoxypropionic acid ethyl, tert-butyl acetate, tert-butyl propionate, propyleneglycol mono tert-butylether acetate, and the like; lactones such as γ-butyllactone and the like. They may be used alone or as a mixture of two or more in combination, but suitable organic solvents are not limited to those described above. Of the organic solvents cited above, however, diethyleneglycol dimethylether, 1-ethoxy-2-propanol, propyleneglycol monomethylether acetate, or a mixture thereof may be preferably used because they allow the most ready dissolution of an acid generator contained in a composition for the formation of a polymer layer.

The use amount of the organic solvent is preferably 200 to 3,000 parts by mass, particularly 400 to 2,500 parts by mass with respect to 100 parts by mass of a polymer.

The polymer layer forming material of the present invention may further include at least one or more nitrogen-containing organic compound(s) as a basic compound.

Suitable such nitrogen-containing organic compounds may include primary, secondary, and tertiary aliphatic amines, heterologous amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, nitrogen-containing alcoholic compounds, amides, imides, carbamates, and the like.

Specifically, suitable primary aliphatic amines may include, for example, ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, tetraethylenepentamine, and the like; suitable secondary aliphatic amines may include, for example, dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethyelenediamine, N,N-dimethyltetraethylenepentamine, and the like; suitable tertiary aliphatic amines may include, for example, trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, N,N,N',N'-tetramethyltetraethylenepentamine, and the like.

Suitable heterologous amines may include, for example, dimethylethylamine, methylethylpropylamine, benzylamine, phenetylamine, benzyldimethylamine, and the like. Specific examples of suitable aromatic amines and heterocyclic amines may include aniline derivatives (for example, aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, N,N-dimethyltoluidine, and the like.) diphenyl(p-tolyl)amine, methyldiphenylamine, triphenylamine, phenylenediamine, naphtylamine, diaminonaphthalene, pyrrole derivatives (for example, pyrrole, 2H-pyrrole, 1-methylpyrrole, 2,4-dimethylpyrrole, 2,5-dimethylpyrrole, N-methylpyrrole, and the like), oxazole derivatives (for example, oxazole, isooxazole, and the like), thiazole derivatives (for example, thiazole, isothiazole, and the like), imidazole derivatives (for example, imidazole, 4-methylimidazole, 4-methyl-2-phenylimidazole, and the like), pyrazole derivatives, furazan derivatives, pyrroline derivatives (for example, pyrroline, 2-methyl-1-pyrroline, and the like), pyrrolidine derivatives (for example, pyrrolidine, N-methylpyrrolidine, pyrrolidinone, N-methylpyrrolidone, and the like), imidazoline derivatives, imidazolidine derivatives, pyridine derivatives (for example, pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, buthoxypyridine, dimethoxypyridine, 4-pyrrolidinopyridine, 2-(1-ethylpropyl)pyridine, aminopyridine, dimethylaminopyridine, and the like), pyridazine derivatives, pyrimidine derivatives, pyrazine derivatives, pyrazoline derivatives, pyrazolidine derivatives, piperidine derivatives, piperadine derivatives, morpholine derivatives, indole derivatives, isoindole derivatives, 1H-indazole derivatives, indolin derivatives, quinoline derivatives (for example, quinoline, 3-quinolinecarbonitrile, and the like), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, uridine derivatives, and the like.

Suitable nitrogen-containing compounds having a carboxyl group may include, for example, aminobenzoic acid, indole-carboxylic acid, amino acid derivatives (for example, nicotinic acid, alanine, arginine, aspartic acid, glutamic acid, glycine, histidine, isoleucine, glycylleucine, leucine, methionine, phenylalanine, threonine, lysine, 3-aminopyradine-2-carboxylic acid, methoxyalanine, and the like). Suitable nitrogen-containing compounds with sulfonyl group may include, for example, 3-pyridine sulfonic acid, p-toluenesulfonic acid pyridinium, and the like. Suitable nitrogen-containing compounds with hydroxyl group or hydroxyphenyl group, or nitrogen-containing alcoholic compounds may include, for example, 2-hydroxypyridine, aminocresol, 2,4-quinolinediol, 3-indolemethanolhydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidineethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxypyrrolidine, 3-quinquelysinol, 3-tropanol, 1-methyl-2-pyrrolidineethanol, 1-aziridineethanol, N-(2-hydroxyethyl)phthalimide, N-(2-hydroxyethyl)isonicotinamide, and the like. Suitable amides may include, for example, formamide, N-methylformamide, N,N-dimethylformamide, acetamide, N-methylacetamide, N,N-dimethylacetamide, propionamide, benzamide, 1-cyclohexylpyrrolidone, and the like. Suitable imides may include, for example, phthalimide, succinimide, maleimide, and the like. Suitable carbamates may include, for example, N-t-butoxycarbonyl-N,N-dicyclohexylamine, N-t-butoxycarbonylbenzimidazol, oxazolidinone, and the like.

Further, the nitrogen-containing organic compounds represented by the following general formula (B)-1 is exemplified.

$$N(X11)_a(Y11)_{3-a} \quad (B)\text{-}1$$

In the formula, a=1, 2, or 3; side-chains X11 may be the same or different, and can be expressed by the following equations (X1) to (X3); side-chains Y11 may be the same or different, and each represents a hydrogen atom, or a linear, branched, or cyclic alkyl group having 1-20 carbon atoms, and may represent an ether group or hydroxyl group, and X11 may be linked to form a ring(s)).

—R2'—O—R3 (X1)

—R4—O—R5—CO—R6 (X2)

—R7—COO—R8 (X3)

In the general formulae (X1) to (X3), R2', R4, and R7 represent a linear or branched alkylene group having 1-4 carbon atoms; R3 and R6 represent a hydrogen atom, or a linear, branched, or cyclic alkyl group having 1-20 carbon atoms, or may comprise one or more of a hydroxyl group, an ether group and an ester group, and a lactone ring.

R5 represents a single bond, or a linear or branched alkylene group having 1-4 carbon atoms, and R8 represents a linear, branched, or cyclic alkyl group having 1-20 carbon atoms, and may include one or more hydroxyl groups, ether groups, ester groups or lactone rings.

Suitable compounds represented by the general formula (B)-1 may include, for example, tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosan, 4,7,13,18-tetraoxa-1,10-diazabicyclo[8.5.5]eicosan, 1,4,10,13-tetraoxa-7,16-diazabicyclooctadecan, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris(2-butyloxyethyl)amine, tris(2-isobutyloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyl)oxyethyl]amine, tris[2-(tert-butoxycarbonylmethyloxy)ethyl]amine, tris(2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxykarbonyl)ethylamine, N,N-bis(2-hydroxyethyl)-2-[(methoxycarbonyl)methoxycarbonyl]ethylamine, N,N-bis(2-acetoxyethyl)-2-[(methoxycarbonyl)methoxycarbonyl]ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofrufryloxycarbonyl)ethylamine, N,N-bis(2-acetoxyethyl)-2-(tetrahydrofurfryloxycarbonyl)ethylamine, N,N-bis(2-hydroxyethyl)-2-[(2-oxotetrahydrofuran-3-il)oxycarbonyl]ethylamine, N,N-bis(2-acetoxyethyl)-2-[(2-oxotetrahydrofuran-3-il)oxycarbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)ethylamine, N,N-bis(2-formyloxyethyl)-2-(2-formyloxyethoxycarbonyl)ethylamine, N,N-bis(2-methoxycarbonyl)-2-(methoxycarbonyl)ethylamine, N-(2-hydroxyethyl)bis[2-(methoxycarbonyl)ethyl]amine, N-(2-acetoxyethyl)bis[2-

(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis[2-(methoxycarbonyl)ethyl]amine, N-(3-acetoxy-1-propyl)bis[2-(methoxycarbonyl)ethyl]amine, N-(2-methoxyethyl)bis[2-(methoxycarbonyl)ethyl]amine, N-butylbis[2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis(methoxycarbonylmethyl)amine, N-hexylbis(methoxycarbonylmethyl)amine, and P-(diethylamino)-δ-valerolactone.

Further, the nitrogen-containing organic compounds having a cyclic structure represented by the following general formula (B)-2 is exemplified.

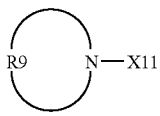

(B)-2

In the formula, X11 is as defined above, R9 represents a linear, or branched alkylene group having 2-20 carbon atoms, and may comprise one or more of a carbonyl group, an ether group, an ester group, and a sulfide group.

Suitable compounds represented by formula (B)-2 may include, for example, 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, acetoxy 2-morpholinoethyl acetate, methoxy 2-(1-pyrrolidinyl)ethyl acetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, 3-(1-pyrrolidinyl)propionic acid methyl, 3-piperidinopropionic acid methyl, 3-morpholinopropionic acid methyl, 3-(thiomorpholino)propionic acid methyl, 2-methyl-3-(1-pyrrolidinyl)propionic acid methyl, 3-morpholinopropionic acid ethyl, 3-piperidinopropionic acid methoxycarbonylmethyl, 3-(1-pyrrolidinyl)propionic acid 2-hydroxyethyl, 3-morpholinopropionic acid 2-acetoxyethyl, 3-(1-pyrrolidinyl)propionic acid 2-oxotetrahydrofuran-3-yl, 3-morpholinopropionic acid tetrahydrofurfryl, 3-piperidinopropionic acid glycidyl, 3-morpholinopropionic acid 2-methoxyethyl, 3-(1-pyrrolidinyl)propionic acid 2-(2-methoxyethoxy)ethyl, 3-morpholinopropionic acid butyl, 3-piperidinopropionic acid cyclohexyl, α-(1-pyrrolidinyl)methyl-γ-butylolactone, β-piperidino-γ-butylolactone, β-morpholino-δ-valerolactone, 1-pyrrolidinylacetic acid methyl, piperidinoacetic acid methyl, morpholinoacetic acid methyl, thiomorpholinoacetic acid methyl, 1-pyrrolidinylacetic acid ethyl, morpholinoacetic acid 2-methoxyethyl, 2-methoxyacetic acid 2-morpholinoethyl, 2-(2-methoxyethoxy)acetic acid 2-morpholinoethyl, 2-[2-(2-methoxyethoxy)ethoxy]acetic acid 2-morpholinoethyl, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Further, the nitrogen-containing organic compounds comprising a cyano group(s) represented by the following general formulae (B)-3 to (B)-6 are exemplified.

(B)-3

(B)-4

(B)-5

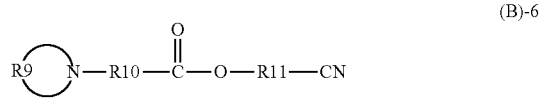

(B)-6

In the formulae, X11, R9, and a are as defined above, R10 and R11 may be the same or different, and represent a linear or branched alkylene group having 1-4 carbon atoms.

Suitable nitrogen-containing compounds comprising the cyano group(s) represented by the general formulae (B)-3 to (B)-6 may include, for example, 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[(2-(methoxymethoxy)ethyl]-3-aminopropiononitrile, N-(2-cyanoethyl)-N-(2-methoxyethyl)-3-aminopropionic acid methyl, N-(2-cyanoethyl)-N-(2-hydroxyethyl)-3-aminopropionic acid methyl, N-(2-acetoxyethyl)-N-(2-cyanoethyl)-3-aminopropionic acid methyl, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, N-cyanomethyl-N-(2-methoxyethyl)-3-aminopropionic acid methyl, N-cyanomethyl-N-(2-hydroxyethyl)-3-aminopropionic acid methyl, N-(2-acetoxyethyl)-N-cyanomethyl-3-aminopropionic acid methyl, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-(cyanomethyl)-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, 3-diethylaminopropionic acid cyanomethyl, N,N-bis(2-hydroxyethyl)-3-aminopropionic acid cyanomethyl, N,N-bis(2-acetoxyethyl)-3-aminopropionic acid cyanomethyl, N,N-bis(2-formyloxyethyl)-3-aminopropionic acid cyanomethyl, N,N-bis(2-methoxyethyl)-3-aminopropionic acid cyanomethyl, N,N-bis[2-(methoxymethoxy)ethyl]-3-aminopropionic acid cyanomethyl, 3-diethylaminopropionic acid (2-cyanoethyl), N,N-bis(2-hydroxyethyl)-3-aminopropionic acid (2-cyanoethyl), N,N-bis(2-formyloxyethyl)-3-aminopropionic acid (2-cyanoethyl), N,N-bis(2-acetoxyethyl)-3-aminopropionic acid (2-cyanoethyl), N,N-bis(2-formyloxyethyl)-3-aminopropionic acid (2-cyanoethyl), N,N-bis(2-methoxyethyl)-3-aminopropionic acid (2-cyanoethyl), N,N-bis[2-(methoxymethoxy)ethyl-3-aminopropionic acid (2-cyanoethyl), 1-pyrrolidinepropionic acid cyanomethyl, 1-piperidinepropionic acid cyanomethyl, 4-morpholinepropionic acid cyanomethyl, 1-pyrrolidinepropionic acid (2-cyanoethyl), 1-piperidinepropionic acid (2-cyanoethyl), and 4-morpholinepropionic acid (2-cyanoethyl).

Further, the nitrogen-containing organic compounds having an imidazole skelton and a polar functional group represented by the following general formula (B)-2 is exemplified.

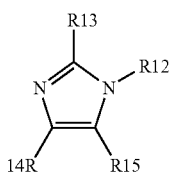

(B)-7

In the formula, R12 represents a linear, branched, or cyclic alkyl group having 2-20 carbon atoms having a polar functional group(s) and comprises one or more of a hydroxyl group, a carbonyl group, an ester group, an ether group, a sulfide group, a carbonate group, a cyano group and an acetal group as the polar functional group(s); R13, R14, and R15 each represent a hydrogen atom, or a linear, branched, or cyclic alkyl group having 1-10 carbon atoms, an aryl group or an aralkyl group).

Further, the nitrogen-containing organic compounds having a benzimidazole skeleton and a polar functional group, and represented by the following general formula (B)-8 is exemplified.

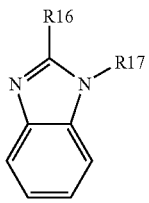

(B)-8

In the formula, R16 represents a hydrogen atom, or a linear, branched, or cyclic alkyl group having 1-10 carbon atoms, an aryl group, or an aralkyl group; R17 represents a linear, branched, or cyclic alkyl group having 1-20 carbon atoms, and comprises, as a polar functional group, one or more of an ester group, an acetal group, and a cyano group, and additionally may comprise, one or more of a hydroxyl group, a carbonyl group, an ether group, a sulfide group, and a carbonate group.

Further, the nitrogen-containing organic compounds having a polar functional group represented by the following general formulae (B)-9 and (B)-10 are exemplified.

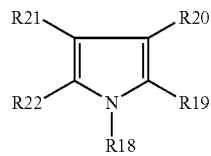

(B)-9

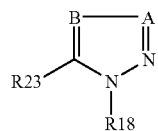

(B)-10

In the formulae, A represents a nitrogen atom or =C—R24; B represents a nitrogen atom or =C—R25; R18 represents a linear, branched, or cyclic alkyl group having 2-20 carbon atoms and having polar functional group, and comprises one or more of a hydroxyl group, a carbonyl group, an ester group, an ether group, a sulfide group, a carbonate group, a cyano group, and an acetal group as the polar functional group; R19, R20, R21, and R22 each represent a hydrogen atom, or a linear, branched, or cyclic alkyl group having 1-10 carbon atoms, or an aryl group, or R19 and R20, and 21 and R22 each may be linked to form a benzene, naphthalene or pyridine ring; R23 represents a hydrogen atom, or a linear, branched, or cyclic alkyl group having 1-10 carbon atoms or an aryl group; R24 and R25 each represent a hydrogen atom, or a linear, branched, or cyclic alkyl group having 1-10 carbon atoms or an aryl group; and R23 and R25 may be linked to form a benzene or naphthalene ring.

Further, the nitrogen-containing organic compounds having an aromatic carboxylic acid ester structure and represented by the following general formulae (B)-11, 12 and 13 are exemplified.

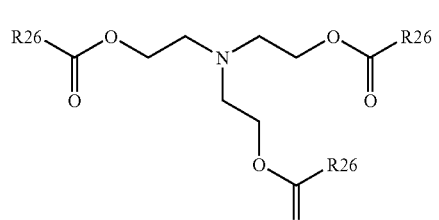

(B)-11

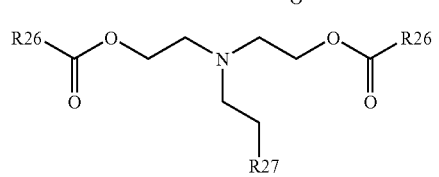

(B)-12

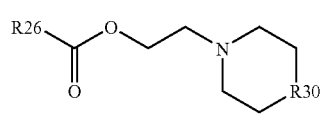

(B)-13

-continued

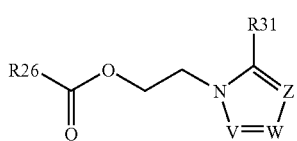
(B)-14

In the formulae, R26 represents an aryl group having 6-26 carbon atoms, or a heterocyclic aromatic group having 4-20 carbon atoms, and part or all of the hydrogen atoms thereof may be substituted with a halogen atom, or a linear, branched or cyclic alkyl group having 1-20 carbon atoms, an aryl group having 6-20 carbon atoms, an aralkyl group having 7-20 carbon atoms, an alkoxy group having 1-10 carbon atoms, an acyloxy group having 1-10 carbon atoms, or an alkylthio group having 1-10 carbon atoms; R28 represents an alkyl group having 1-10 carbon atoms part of whose methylene groups may be substituted with an oxygen atom; R29 represents an alkyl or acyl group having 1-10 carbon atoms part of whose methylene groups may be substituted with an oxygen atom; R30 represents a single-bond, a methylene group, an ethylene group, a sulfur atom, or —O(CH$_2$CH$_2$O)$_a$— group; a is 0, 1, 2, 3, or 4; R31 represents a hydrogen atom, or a methyl group, an ethyl group, or a phenyl group; V is a nitrogen atom, or CR32; W is a nitrogen atom, or CR33; Z is a nitrogen atom, or CR34; and R32, R33, and R34 represent, independently of each other, a hydrogen atom, or a methyl group or a phenyl group, or R32, R33, and R34 may be linked to form an aromatic ring having 6-20 carbon atoms, or a heterocyclic aromatic ring having 2-20 carbon atoms.

Further, the nitrogen-containing organic compounds having a 7-oxanorbornan-2-carboxylate ester structure and represented by the following general formula (B)-15 is exemplified.

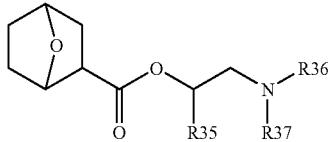
(B)-15

In the formula, R35 represents a hydrogen atom, or a linear, branched, or cyclic alkyl group having 1-10 carbon atoms; R36 and R37 independently represent an alkyl group having 1-20 carbon atoms, an aryl group having 6-20 carbon atoms, or an aralkyl group having 7-20 carbon atoms wherein the group may comprise one or more of polar functional groups such as ether, carbonyl, ester, alcohol, sulfide, nitrile, amine, imine, amide and the like, and wherein part of the hydrogen atoms may be substituted with a halogen atom; or R36 and R37 may be linked to form a heterocyclic, or heterocyclic aromatic ring having 2-20 carbon atoms.

The addition amount of the nitrogen-containing compound is preferably 0.001 to 2 parts, particularly 0.01 to 1 part by mass with respect to 100 parts by mass of a polymer. When added at 0.001 part by mass or more, the nitrogen-containing compound will exhibit a sufficient effect to be expected therefrom. When added at 2 parts by mass or less, the nitrogen-containing compound will scarcely degrade the sensitivity of the polymer.

The polymer layer forming material of the present invention may include, in addition to the above-described additives, a surfactant as an additive optionally selected to improve the coating performance of the material. It should be noted that the addition amount of this optionally selected additive should be kept within a normal range which will not interfere with the effect of the present invention.

Preferred surfactants are non-ionic ones, and may include perfluoroalkylpolyoxyethylene ethanols, alkylester fluorides, perfluoroalkylamine oxides, EO attached perfluoroalkyls, fluorine-containing organosiloxane compounds, and the like. For example, suitable surfactants may include, Fluorad "FC-430," "FC-431," and "FC-4430," (manufactured by Sumitomo 3M); Surflon "S-141," "S-145," "KH-10," "KH-20," "KH-30," and "KH-40" (manufactured by Asahi Glass); Unidyne "DS-401," "DS-403," and "DS-451" (manufactured by Daikin Industry); Megaface "F-8151" (manufactured by Dainippon Ink); and "X-70-092," and "X-70-093" (manufactured by Shin-Etsu Chemical Co., Ltd.). Among the surfactants, Fluorad "FC-4430" (Sumitomo 3M), "KH-20," and "KH-30" (manufactured by Asahi Glass), and "X-70-093" (Shin-Etsu Chemical Co., Ltd.) are particularly preferred.

It is preferably to perform heating treatment after the polymer layer forming material is used for forming a polymer layer containing a photoacid generator. Through this treatment, it is possible to vaporize the solvent, thereby firmly stabilizing the material onto the surface of a substrate, which will facilitate the handling of the substrate in later operations particularly during exposure to light.

Then, a high energy beam is radiated, for example, through a mask onto the surface of a substrate, or a laser beam is scanned as appropriate over the surface, to illumine the surface in the form of a pattern. Through this operation, it is possible to generate acid at the polymer layers of illumined positions. Acid generated at the polymer layer of each illumined position acts, at the underlying monomolecular film, on a hydroxyl group precursor functional group represented by X to convert it into a hydroxyl group. Through this operation, it is possible to obtain a site-selectively distributed array of positions each of which contains hydroxyl group.

Then, it is possible to attach, to the hydroxyl group generated through the step of converting a hydroxyl group precursor functional group of a silane compound into a hydroxyl group in a dehydrated environment, a mononucleotide which has its 5'-end protected with an acid leaving group and 3'-end with phosphoramidite attached, and converting the acid leaving group attached to the 5'-end into a hydroxyl group using a photoacid generator as described above contained in a polymer layer. As seen from above, it is possible to utilize the method for making a microarray of the present invention so as to extend the length of an oligonucleotide chain.

It is preferred to introduce the heating treatment after the radiation of a high energy beam, because then it is possible to complete the reaction of a hydroxyl group precursor functional group with generated acid, or to facilitate the reaction.

It is preferred to select a high energy beam having a wavelength in the range of 250 nm to 400 nm, because then it will be possible to greatly reduce the risk of disrupting the coupling of a silane compound forming a monomolecular film with the substrate, thereby minimizing the escape of the silane compound from the substrate.

Afterwards, when the polymer layer is removed by any conventional method, a substrate for making a microarray will be obtained which has hydroxyl group distributed on its surface site-selectively in the form of a pattern.

EXAMPLES

The present invention will be illustrated below with reference to examples, but it should be understood that the present invention is not limited to those examples.

Production Example 1

Production of 10-(methoxymethoxy)decyltrimethoxysilane

Under a nitrogen atmosphere, 64 g of trimethoxysilane and 0.57 g of acetic acid were dropped in a mixture of 100 g of 10-(methoxymethoxy)-1-decene and a catalytic amount of a solution of platinate chloride in tetrahydrofuran at 80° C. The reaction mixture was stirred at 80° C. for 3 hours, and distilled under reduced pressure to yield 131 g of a target compound.
10-(Methoxymethoxy)decyltrimethoxysilane
Boiling point: 142° C./66 Pa
IR (liquid film)vmax: 2927, 2854, 2840, 1465, 1191, 1143, 1089, 1049 cm$^{-1}$
$^{13}$C-NMR (150 MHz, CDCl$_3$) δ: 9.10, 22.55, 26.18, 29.19, 29.39, 29.56, 29.71, 33.09, 50.44, 55.03, 67.84, 96.34 ppm
$^{1}$H-NMR (600 MHz, CDCl$_3$) δ: 0.59-0.62 (2H, m), 1.21-1.39 (14H, m), 1.52-1.57 (2H, quintet-like), 3.32 (3H, s), 3.48 (2H, t, J=7 Hz), 3.53 (9H, s), 4.58 (2H, s) ppm.

Production Example 2

Preparation of a Monomolecular Film Forming Material Solution

A 2.1 g of 10-(methoxymethoxy)decylmethoxysilane obtained in Example 1 and 5.9 g of hexyltrimethoxysilane were dissolved in 4% dichloromethane-hexane to 1 liter which was used as a monomolecular film forming material solution.

Production Example 3

Preparation of a Polymer

Monomer components necessary for the preparation of a polymer used for the formation of a polymer layer were combined, and allowed to copolymerize in a solvent of isopropylalcohol, and the polymer was crystallized in hexane. The polymer was washed with hexane repeatedly, isolated, and dried to give polymer 1 whose composition is as given below. The composition of the polymer was confirmed by $^{1}$H-NMR, and its molecular weight and dispersive power by gel permeation chromatography.
Polymer 1
Molecular weight (Mw)=7,300
Dispersion degree (Mw/Mn)=1.67 polymer 1

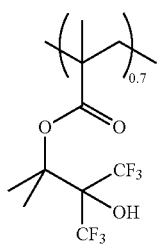

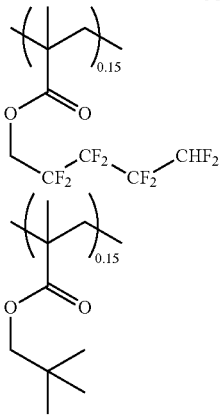

Production Example 4

Preparation of a Polymer Layer Forming Material

Polymer 1 80 parts by mass, and a photoacid generator (CGI-1397 from Chiba Specialty Chemicals; a compound represented by the general formula (3) above where R$_2$ is n-propyl) 6 parts by mass were dissolved in 1-methoxyisopropyl acetate 720 parts by mass, and the mixture was filtered to give a solution which was used for the formation of a polymer layer.

Production Example 5

Production of a Polymer for Resist t-Butoxystyrene: 1-ethylcyclopentylmethacrylate: β-methacryloyloxy-γ-butyllactone=30: 10: 60
A 17.6 g of t-butoxystyrene, 18.2 g of 1-ethylcyclopentylmethacrylate, and 17.0 g of β-methacryloyloxy-γ-butyllactone were dissolved to 1100 g of methylisobutylketone, to which was added 1.3 g of AIBN, and the mixture was heated at 80° C. for 8 hours. The resulting mixture was poured into a bulk of hexane to precipitate. The precipitate was dissolved in a small amount of methylisobutylketone, which was then precipitated through its renewed immersion in a bulk of hexane. Through these procedures was obtained a copolymer having a composition as described above that has a weight-average molecular weight of about 8000 and dispersive power of 2.0.

Production Example 6

Preparation of a Resist Composition

A mixture comprising (t-butoxystyrene: 1-ethylcyclopentylmethacrylate: β-methacryloyloxy-γ-butyllactone=30: 10: 60) 80 parts by mass, triphenylsulfonium p-toluenesulfonate 6 parts by mass, and tributylamine 0.5 part by mass was dissolved in PGMEA 720 parts by mass, and the mixture was filtered to give a solution which was used as a resist composition.

(Manufacture of a substrate for making a microarray: Example 1

Onto a substrate 1a to be processed, a solution prepared as in Production Example 6 for the formation of a resist was coated by spin-coating, and heated at 100° C. for 90 sec for pre-baking, to form a resist film 1b having a thickness of 0.3 µm on the substrate (FIG. 1(1)).

Then, a KrF excimer laser 2d was radiated through a mask pattern 2c onto the resist film 1b so that specified positions of the film upon which a monomolecular film will be formed can be irradiated with the beam (FIG. 1(2)). After the exposure to light, the substrate was heated at 110° C. for 90 sec for post-baking. Then, a 2.38% TMAH aqueous solution was applied for etching and thus a resist pattern was obtained that consisted of apertures formed at the specified positions upon which a monomolecular film will be formed (FIG. 1(3)).

Next, the substrate 1a was immersed for 3 minutes in a solution 4e for the formation of a monomolecular film prepared as in Production Example 2 (FIG. 1(4)), to form a monomolecular film 5f (FIG. 1(5)).

To the substrate having received the above immersion treatment, a material for the formation of a polymer layer prepared as in Production Example 4 was applied by spin coating, and subjected to pre-baking to form a polymer layer 6g having 0.3 µm thick (FIG. 1(6)).

Then, onto the polymer layer 6g, an i-beam 7i (365 nm) was radiated through a patterned mask 7h so that a site in which hydroxyl group should be developed can be irradiated by the beam (FIG. 1(7)). Afterwards, the substrate was heated at 100° C. for 5 minutes for post-baking (FIG. 1(8)). Through this operation, acid was generated at each polymer layer 7j exposed to the i-beam, and acid thus generated acted on methoxymethoxy group in the underlying monomolecular film at the site 8k to convert it into hydroxyl group (FIG. 1(8)).

Next, the polymer layer 8g was removed by washing the substrate with 1-methoxyisopropyl acetate and acetone (FIG. 1(9)).

In addition, the substrate 9a treated as above was immersed in propyleneglycol monomethylether to remove the resist film 9b (FIG. 1(10)).

As a result, a substrate 10a for microarray was obtained that has, at each position 10k specified for the immobilization of a detection material, a monomolecular film 10f formed which has silicon oxide chains as a functional group for the immobilization of hydroxyl group.

Examples 2 to 7, and Comparative Examples 1 to 6

Polymer layer forming materials were prepared as in Production Example 4, except that as the photoacid generator, compounds represented by the general formula (3) where $R_2$ is n-propyl group (photoacid generator 1), p-methylphenyl group (photoacid generator 2), or di(4-tert-butylphenyl)iodonium 4-methylphenylsulfonate (photoacid generator 3) were used in such an amount as to give the concentrations of the respective compounds as described in Table 1 below (Examples 2 to 7, and Comparative Examples 1 to 3). The solvent was propyleneglycol. Table 2 shows the solubility of the respective compounds 24 hours after the mixture.

TABLE 1

|  | 0.025 mole/kg | 0.050 mole/kg | 0.144 mole/kg |
| --- | --- | --- | --- |
| photoacid generator 1 | Example 2 | Example 3 | Example 4 |
| photoacid generator 2 | Example 5 | Example 6 | Example 7 |
| photoacid generator 3 | Comp. Ex. 1 | Comp. Ex. 2 | Comp. Ex. 3 |

TABLE 2

|  | Solubility |
| --- | --- |
| Example 2 | o |
| Example 3 | o |
| Example 4 | o |
| Example 5 | o |
| Example 6 | o |
| Example 7 | o |
| Comparative Example 1 | x |
| Comparative Example 2 | x |
| Comparative Example 3 | x |

As seen from Table 2, compositions prepared in Examples 2 to 7 readily dissolved without forming any solid precipitates, while compositions prepared in Comparative Examples 1 to 3 exhibited solid precipitates. In view of this, the composition of photoacid generator 3 was varied as shown in Table 3 (Comparative Examples 4 to 6), and the solvent was replaced with ethyl lactate. Then, the compositions were found to dissolve without forming any solid precipitates. In Table 2, o represents the composition is soluble without forming any solid precipitates, while x represents the presence of solid precipitates.

TABLE 3

|  | 0.025 mole/kg | 0.050 mole/kg | 0.144 mole/kg |
| --- | --- | --- | --- |
| photoacid generator 3 | Comp. Ex. 4 | Comp. Ex. 5 | Comp. Ex. 6 |
| Solubility | o | o | o |

Next, onto a substrate which has a monomolecular film consisting solely of 10-(methoxymethoxy)dodecyltrimethoxysilane, reaction solutions prepared as in Examples 2 to 7 and in Comparative Examples 4 to 6 described above were applied by spin-coating.

Immediately thereafter, the substrate was heated at 80° C. for 5 minutes for pre-baking, to form a polymer layer 0.3 µm thick on the tope of the monomolecular film.

An i-beam was radiated onto the polymer layer at 2000 mJ/cm$^2$, and the substrate was heated at 80° C. for 20 minutes for post-baking. Immediately, the substrate had THF poured on its surface to remove the polymer layer therefrom, and subjected to spin-drying, and received water on its surface for contact angle measurement (change in surface contact angle was determined before and after the heating treatment consisting of heating in a mixture of hydrochloride/methanol at 60° C. for 30 minutes). The results are shown in Table 4. The surface contact angle was 73 degree before the reaction and 62 degree after the reaction.

TABLE 4

|  | Contact angle | Decrement | Reaction |
| --- | --- | --- | --- |
| Example 2 | 67° | −6° | present |
| Example 3 | 67° | −6° | present |
| Example 4 | 67° | −6° | present |
| Example 5 | 62° | −11° | completed |
| Example 6 | 62° | −11° | completed |
| Example 7 | 62° | −11° | completed |
| Comparative Example 4 | 73° | 0° | absent |
| Comparative Example 5 | 73° | 0° | absent |
| Comparative Example 6 | 73° | 0° | absent |

From this, it was found that the compositions from Examples 4 to 6 which should generate acid in the same manner reacted similarly, while, in contrast, the compositions from Comparative Examples 4 to 6 scarcely reacted, and thus it was concluded that the compositions from Comparative Examples 4 to 6 did not generate acid.

The present invention is not limited to the above embodiments. The above embodiments are exemplifications. Any of those which have substantially the same constitution and have the same effects as technical ideas described in claims of the present invention are included in the technical scope of the present invention.

The invention claimed is:

1. A method for manufacturing a substrate for making a microarray, comprising at least the steps of:
    forming a monomolecular film on the surface of a substrate using a silane compound represented by the following general formula (1),

$Y_3Si-(CH_2)_m-X$ (1), wherein m represents an integer from 3 to 20; X represents a hydroxyl group precursor functional group which will be converted to a hydroxyl group when exposed to acid; and Y independently represents a halogen atom or an alkoxy group having 1-4 carbon atoms; and
    converting the hydroxyl group precursor functional group represented by X to a hydroxyl group, wherein the step of converting the hydroxyl group precursor functional group represented by X to a hydroxyl group comprises forming, on the monomolecular film, a polymer layer containing a compound represented by the following general formula (2), (2)

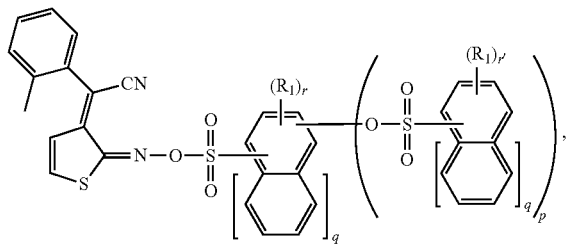

wherein $R_1$ may be the same or different, and represents a hydrogen atom, a fluorine atom, a chlorine atom, a nitro group, or a linear, branched, or cyclic alkyl group or alkoxy group having 1-12 carbon atoms substituted or unsubstituted; q independently represents 0 or 1; p is 1 or 2; r is an integer from 0 to 4; and r' is an integer from 0 to 5; or a compound represented by the following general formula (3), (3)

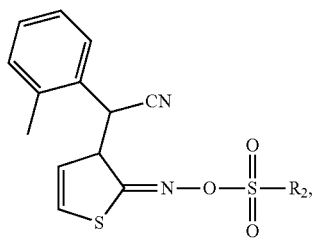

wherein $R_2$ represents a linear, branched, or cyclic alkyl group or alkoxy group having 3-10 carbon atoms substituted or unsubstituted, or a substituted or unsubstituted phenyl group or camphor; and radiating a high energy beam onto the substrate in the form of a pattern.

2. The method for manufacturing a substrate for making a microarray according to claim 1, wherein the hydroxyl group precursor functional group represented by X in the general formula (1) is an alkoxymethoxy group in which the alkoxy group moiety has 1-6 carbon atoms and/or an oxyranyl group.

3. The method for manufacturing a substrate for making a microarray according to claim 1, wherein the step of forming a monomolecular film using a silane compound represented by the general formula (1) comprises mixing the silane compound with at least one or more of silane compounds represented by the following general formulae (4) and (5),

$Y'_3Si-(CH_2)_n-CH_3$ (4)

$Y'_3Si-(CH_2)_n-OCH_3$ (5), wherein n is an integer from 0 to (m-2), m is as defined in relation to the general formula (1); and Y' represents a halogen atom or an alkoxy group having 1-4 carbon atoms; and
    using the resulting mixture to form the monomolecular film.

4. The method for manufacturing a substrate for making a microarray according to claim 2, wherein the step of forming a monomolecular film using a silane compound represented by the general formula (1) comprises mixing the silane compound with at least one or more of silane compounds represented by the following general formulae (4) and (5),

$Y'_3Si-(CH_2)_n-CH_3$ (4)

$Y'_3Si-(CH_2)_n-OCH_3$ (5), wherein n is an integer from 0 to (m-2), m is as defined in relation to the general formula (1); and Y' represents a halogen atom or an alkoxy group having 1-4 carbon atoms; and
    using the resulting mixture to form the monomolecular film.

5. The method for manufacturing a substrate for making a microarray according to claim 1, wherein the step of converting the hydroxyl group precursor functional group to a hydroxyl group comprises, in sequence, forming polymer layer comprising a photoacid generator on the substrate and then subjecting the substrate to heating treatment, radiating a high energy beam onto the substrate in the form of a pattern, and then subjecting the substrate to heating treatment, and then removing the polymer layer.

6. The method for manufacturing a substrate for making a microarray according to claim 2, wherein the step of converting the hydroxyl group precursor functional group to a hydroxyl group comprises, in sequence, forming polymer layer comprising a photoacid generator on the substrate and then subjecting the substrate to heating treatment, radiating a high energy beam onto the substrate in the form of a pattern, and then subjecting the substrate to heating treatment, and then removing the polymer layer.

7. The method for manufacturing a substrate for making a microarray according to claim 3, wherein the step of converting the hydroxyl group precursor functional group to a hydroxyl group comprises, in sequence, forming polymer layer comprising a photoacid generator on the substrate and then subjecting the substrate to heating treatment, radiating a high energy beam onto the substrate in the form of a pattern, and then subjecting the substrate to heating treatment, and then removing the polymer layer.

8. The method for manufacturing a substrate for making a microarray according to claim 4, wherein the step of converting the hydroxyl group precursor functional group to a hydroxyl group comprises, in sequence, forming polymer layer comprising a photoacid generator on the substrate and then subjecting the substrate to heating treatment, radiating a high energy beam onto the substrate in the form of a pattern, and then subjecting the substrate to heating treatment, and then removing the polymer layer.

9. The method for manufacturing a substrate for making a microarray according to claim 1, wherein the high energy beam has a wavelength in the range of 250 nm to 400 nm.

10. The method for manufacturing a substrate for making a microarray according to claim 2, wherein the high energy beam has a wavelength in the range of 250 nm to 400 nm.

11. The method for manufacturing a substrate for making a microarray according to claim 3, wherein the high energy beam has a wavelength in the range of 250 nm to 400 nm.

12. The method for manufacturing a substrate for making a microarray according to claim 4, wherein the high energy beam has a wavelength in the range of 250 nm to 400 nm.

13. The method for manufacturing a substrate for making a microarray according to claim 1, wherein the microarray is used for analyses of biomolecules.

14. The method for manufacturing a substrate for making a microarray according to claim 2, wherein the microarray is used for analyses of biomolecules.

15. The method for manufacturing a substrate for making a microarray according to claim 3, wherein the microarray is used for analyses of biomolecules.

16. The method for manufacturing a substrate for making a microarray according to claim 4, wherein the microarray is used for analyses of biomolecules.

17. The method for manufacturing a substrate for making a microarray according to claim 1, wherein, the method further contains a step that on the substrate in which the hydroxyl group generated through the step of converting the hydroxyl group precursor functional group to a hydroxyl group has been attached, in a dehydrated environment, a mononucleotide which has its 5'-end protected with an acid leaving group and 3'-end with phosphoramidite attached, the acid leaving group of the 5'-end is converted into a hydroxyl group using the photoacid generator contained in the polymer layer.

18. The method for manufacturing a substrate for making a microarray according to claim 2, wherein, the method further contains a step that on the substrate in which the hydroxyl group generated through the step of converting the hydroxyl group precursor functional group to a hydroxyl group has been attached, in a dehydrated environment, a mononucleotide which has its 5'-end protected with an acid leaving group and 3'-end with phosphoramidite attached, the acid leaving group of the 5'-end is converted into a hydroxyl group using the photoacid generator contained in the polymer layer.

19. The method for manufacturing a substrate for making a microarray according to claim 3, wherein, the method further contains a step that on the substrate in which the hydroxyl group generated through the step of converting the hydroxyl group precursor functional group to a hydroxyl group has been attached, in a dehydrated environment, a mononucleotide which has its 5'-end protected with an acid leaving group and 3'-end with phosphoramidite attached, the acid leaving group of the 5'-end is converted into a hydroxyl group using the photoacid generator contained in the polymer layer.

20. The method for manufacturing a substrate for making a microarray according to claim 4, wherein, the method further contains a step that on the substrate in which the hydroxyl group generated through the step of converting the hydroxyl group precursor functional group to a hydroxyl group has been attached, in a dehydrated environment, a mononucleotide which has its 5'-end protected with an acid leaving group and 3'-end with phosphoramidite attached, the acid leaving group of the 5'-end is converted into a hydroxyl group using the photoacid generator contained in the polymer layer.

21. The method for manufacturing a substrate for making a microarray according to claim 17, wherein the acid leaving group for protecting the 5'-end of the nucleotide is a dimethoxytrityl group.

22. The method for manufacturing a substrate for making a microarray according to claim 18, wherein the acid leaving group for protecting the 5'-end of the nucleotide is a dimethoxytrityl group.

23. The method for manufacturing a substrate for making a microarray according to claim 19, wherein the acid leaving group for protecting the 5'-end of the nucleotide is a dimethoxytrityl group.

24. The method for manufacturing a substrate for making a microarray according to claim 20, wherein the acid leaving group for protecting the 5'-end of the nucleotide is a dimethoxytrityl group.

\* \* \* \* \*